United States Patent [19]

Psarras

[11] 4,181,678

[45] Jan. 1, 1980

[54] SYMMETRICAL PERFLUOROALKYLENE OXIDE α,ω-DIACYL FLUORIDES

[75] Inventor: Theodore Psarras, Gainesville, Fla.

[73] Assignee: The United States of America as represented by the Secretary of the Air Force, Washington, D.C.

[21] Appl. No.: 942,571

[22] Filed: Sep. 15, 1978

[51] Int. Cl.$^2$ ................ C07C 53/20; C07C 51/58
[52] U.S. Cl. .................................................. 260/544 F
[58] Field of Search ..................... 260/544 F, 543 F

[56] References Cited

U.S. PATENT DOCUMENTS

| | | | |
|---|---|---|---|
| 3,250,806 | 5/1966 | Warnell | 260/535 |
| 3,317,484 | 5/1967 | Fritz | 260/78.4 |
| 3,318,911 | 5/1967 | Takehara et al. | 260/340.7 |
| 3,862,971 | 1/1975 | Rudolph et al. | 260/408 |

Primary Examiner—Gerald A. Schwartz
Attorney, Agent, or Firm—Joseph E. Rusz; Cedric H. Kuhn

[57] ABSTRACT

Symmetrical perfluoroalkylene oxide α,ω-diacyl fluoride is prepared by reacting a perfluoroalkylene oxide, α, ω-diiodide with fuming sulfuric acid in the presence of zinc sulfate while adding chlorine.

5 Claims, No Drawings

SYMMETRICAL PERFLUOROALKYLENE OXIDE α,ω-DIACYL FLUORIDES

RIGHTS OF THE GOVERNMENT

The invention described herein may be manufactured and used by or for the Government of the United States for all governmental purposes without the payment of any royalty.

FIELD OF THE INVENTION

This invention relates to symmetrical perfluoroalkylene oxide α,ω-diacyl fluorides. In one aspect, it relates to a process for preparing the diacyl fluorides.

BACKGROUND OF THE INVENTION

As disclosed in U.S. Pat. Nos. 3,250,806 and 3,317,484, perfluoroalkylene oxide diacyl fluorides can be prepared by the addition of tetrafluoroethylene oxide (TFEO) to diacyl fluorides. The diacyl fluoride prepared by addition of TFEO to oxalyl fluoride has a symmetrical structure as shown by the following equation:

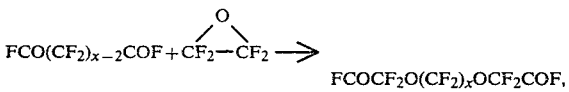

$$FCOCF_2O(CF_2)_xOCF_2COF,$$

where x equals 2 (oxalyl fluoride). However, the characteristics of this reaction are such that this method of preparation becomes synthetically unattractive. When the diacyl fluoride used in the foregoing addition reaction is one in which the value of x in the formula $FCO(CF_2)_{x-2}COF$ is greater than 2, e.g., x equals 5 [hexafluoroglutaryl fluoride (HFGF)], the product obtained has the unsymmetrical structure $FCO(CF_2)_4OCF_2CF_2OCF_2COF$. In the literature there is no disclosure of a method whereby the symmetrical isomer $FCOCF_2O(CF_2)_5OCF_2COF_2$ can be synthesized.

U.S. Pat. No. 3,862,971 discloses a process for preparing perfluorinated carboxylic acids and their fluorides. In accordance with this process a fluoroalkyl iodide of the formula $R_f(CF_2CF_2)_nI$, where $R_f$ is perfluoroalkyl, is reacted with oleum in the presence of a metal salt while adding chlorine. The patent does not teach a method for the preparation of symmetrical perfluoroalkylene oxide α,ω-diacyl fluorides.

A large amount of research work has been conducted with the object of providing monomers that can be used in synthesizing elastomeric polymers suitable for various aerospace applications. Because of their outstanding thermal, oxidative and chemical stability, much of the work has been directed toward the preparation of fluorocarbon polymers for use in aerospace seal and sealant applications. Perfluoroalkylene oxide diacyl fluorides have been used as intermediates in the synthesis of imidate and thioimidate ester monomers for use in preparing elastomeric polymers which are useful for such applications. It would be desirable to have symmetrical perfluoroalkylene oxide diacyl fluorides for use in preparing monomers to be employed in the preparation of fluorocarbon polymers.

It is an object of this invention, therefore, to provide symmetrical perfluoroalkylene oxide α,ω-diacyl fluorides.

Another object of the invention is to provide a process for preparing symmetrical perfluoroalkylene oxide α,ω-diacyl fluorides.

Other objects and advantages of the invention will become apparent to those skilled in the art upon consideration of the accompanying disclosure.

SUMMARY OF THE INVENTION

In one embodiment, the present invention resides in a process for synthesizing symmetrical perfluoroalkylene oxide α,ω-diacyl fluorides. According to the process, a perfluoroalkylene oxide α,ω-diiodide having the formula $CF_2ICF_2O(CF_2)_xOCF_2CF_2I$, where x is an integer equal to at least 2, e.g., an integer in the range of 2 to 10, inclusive, is reacted with fuming sulfuric acid in the presence of zinc sulfate while adding chlorine. The reaction involved in carrying out the process can be represented by the following equation:

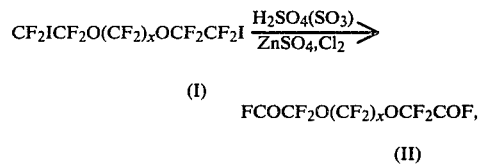

(I)

$$FCOCF_2O(CF_2)_xOCF_2COF,$$

(II)

where x is as defined above.

As mentioned hereinabove, when using a diacyl fluoride having the formula $FOC(CF_2)_{x-2}COF$, where x is greater than 2, in the conventional process for preparing perfluoroalkylene oxide α,ω-diacyl fluorides, the product obtained has either an unsymmetrical structure or is a mixture of both the symmetrical and unsymmetrical structures. The present process is, therefore, particularly applicable to the preparation of diacyl fluorides (II) in which x has a value greater than 2. Furthermore, in another embodiment, the present invention resides in a symmetrical perfluoroalkylene α,ω-diacyl fluoride according to formula (II) in which x is greater than 2, e.g., an integer in the range of 3 to 10, inclusive.

In a preferred procedure for carrying out the present process, a mixture of the diiodide (I) and the zinc sulfate catalyst is initially heated to a temperature in the range of about 60 to 110° C. The fuming sulfuric acid is then added while at the same time bubbling chlorine through the reaction mixture. After addition of the sulfuric acid is completed, the flow of chlorine is continued for a period of about 30 minutes to 1 hour while maintaining the temperature of the reaction mixture in the aforementioned temperature range. The total reaction period usually ranges from about 2 to 8 hours. At the end of the reaction period, the reaction mixture is cooled to ambient temperature whereupon the product of the process separates as a layer on top of a green-colored sulfuric acid layer. The product layer is then recovered, e.g., by decantation, and subjected to distillation to give a purified symmetrical diacyl fluoride (II).

The fuming sulfuric acid generally contains about 65 weight percent free sulfur trioxide. However, it is to be understood that fuming sulfuric acid containing other concentrations of free $SO_3$ can be utilized. In general, a molar excess of free $SO_3$ as compared to diiodide (I) is employed. Thus, the mole ratio of free $SO_3$ to diiodide (I) is usually about 8 to 20:1.

In general, a catalytic amount of zinc sulfate is used in the process. While the actual amount employed can vary over a relatively wide range, the amount usually ranges from about 0.5 to 5 weight percent, based upon the weight of the diiodide (I).

The amount of chlorine added during conduct of the process can also vary within rather broad limits. The amount usually ranges from about 5 to 20 weight percent, based upon the weight of the diiodide (I).

The diiodide (I) used in the process is prepared by addition of tetrafluoroethylene to a mixture of an acyl fluoride, potassium fluoride and iodine monochloride. The acyl fluorides can be represented by the formula $FCO(CF_2)_{x-2}COF$, where x is an integer equal to at least 2, e.g., an integer ranging from 2 to 10, inclusive. Examples of the acyl fluorides include oxalyl difluoride and difluorides of perfluoromalonic acid, perfluorosuccinic acid, perfluoroglutaric acid, perfluoroadipic acid, perfluoropimelic acid, perfluoroazelaic acid, perfluorosebacic acid, and the like.

In a preferred procedure for preparing the diiodide (I), potassium fluoride is initially dried in an appropriate reaction vessel at an elevated temperature under vacuum. After cooling to room temperature, the acyl fluoride and a solvent, such as diglyme, are charged to the vessel. The resulting mixture is stirred until the exothermic reaction subsides and most of the potassium fluoride is dissolved. The mole ratio of potassium fluoride to acyl fluoride is generally at least 2 to 1. The reaction mixture is then cooled in an ice bath after which the iodine monochloride is added. The mole ratio of iodine monochloride to acyl fluoride is also usually at least 2 to 1. After allowing the mixture to warm to room temperature while stirring, the reaction vessel is connected to a tetrafluoroethylene cylinder. Tetrafluoroethylene is then pressured into the vessel until the rate of take-up is negligible. Excess tetrafluoroethylene is then vented and the reaction mixture is distilled to give the diiodide (I).

The symmetrical perfluoroalkylene oxide $\alpha,\omega$-diacyl fluorides are particularly useful as intermediates for synthesizing perfluoroalkylene ether imidate and thioimidate esters. The latter compounds are useful as monomers in preparing perfluoroalkylene ether bibenzoxazole polymers. In synthesizing the imidate and thioimidate esters, initially perfluoroalkylene ether dinitriles are prepared from the diacyl fluorides by amidation and dehydration with phosphorus pentoxide. The procedure for preparing the dinitriles is described in more detail in U.S. Pat. No. 3,317,484. The dinitriles are converted to imidate or thioimidate esters by reacting same with an excess of ethanethiol or trifluoroethanol in the presence of a catalytic amount of triethylamine. A detailed discussion of the synthesis of perfluoroalkylene ether imidate and thioimidate esters is included in U.S. Pat. No. 4,053,498.

The imidate and thioimidate esters, prepared as described above using the diacyl fluorides (II) as starting materials, are reacted with fluorocarbon ether bis(o-aminophenol) monomers to provide linear fluorocarbon ether bibenzoxazole polymers. Examples of fluorocarbon ether bis(o-aminophenol) monomers include 1,11-bis(3-amino-4-hydroxyphenyl)perfluoro-3,9-dioxaundecane, 1,14-bis(3-amino-4-hydroxyphenyl)perfluoro-5,10-dimethyl-3,6,9,15-tetraoxatetradecane, and 1,17-bis(3-amino-4-hydroxyphenyl)perfluoro-3,6,9,15-tetraoxaheptadecane. The polymers are elastomeric, have a low glass transition temperature, and are oxidatively stable at elevated temperatures. The polycondensation reaction is generally conducted in hexafluoroisopropanol at about 50° to 55° C. in the presence of four molar equivalents of glacial acetic acid.

A more comprehensive understanding of the invention can be obtained by referring to the following illustrative examples which are not intended, however, to be unduly limitative of the invention.

EXAMPLE I

Preparation of $CF_2ICF_2O(CF_2)_5OCF_2CF_2I$

Potassium fluoride (25 g, 0.43 mole) was charged into a 500-ml Fischer-Porter pressure bottle and dried over night at 200° C. under vacuum. After cooling to room temperature, diglyme (200 ml) and hexafluoroglutaryl fluoride (HFGF) $[FCO(CF_2)_{x-2}COF$, where x=5] were charged to the bottle and the resulting mixture was stirred for one hour. At the end of this period, the exothermic reaction had subsided and most of the potassium fluoride had been dissolved. The reaction mixture was cooled in an ice bath and iodine monochloride (26 ml, $\simeq 0.5$ mole) was added through a syringe. The mixture was stirred and allowed to warm to room temperature.

The bottle was connected to a tetrafluoroethylene (TFE) cylinder through a copper tubing manifold and TFE was pressured in at 60 psi. The progress of the reaction was followed by the drop in pressure and more TFE was added until the take-up rate was negligible. At this point the color of the reaction mixture had changed to light pink yellow from the originally deep red color. After excess TFE was vented, the reaction mixture was poured into water and decolorized with $Na_2S_2O_3$. The crude product was separated as the heavy phase. The crude product was washed repeatedly with a 5% solution of $NaHCO_3$, dried and distilled.

Several runs were made in accordance with the foregoing procedure, using a total of 440 g (1.8 moles) of HFGF. Distillation gave the diiodide (99.8% purity) in 36.7% average conversion.

EXAMPLE II

Preparation of $CF_2ICF_2OCF_2CF_2OCF_2CF_2I$

Potassium fluoride (55 g, 1.0 mole) was charged to a Fischer-Porter pressure bottle and dried over night at 200° C. under vacuum. After the bottle was cooled to room temperature, tetraglyme (200 ml) was added and the mixture was stirred for a few minutes under vacuum.

The reaction vessel was cooled in a Dry Ice-acetone bath and oxalyl fluoride [FCOCOF] (45 g, 0.48 mole) was charged through a vacuum manifold. The mixture was allowed to warm to ambient temperature and stirred for one hour. The reaction vessel was cooled in a Dry Ice-acetone bath, iodine monochloride (50 ml, 1.0 mole) was added through a syringe and the system evacuated. The reaction vessel was connected through copper tubing to a cylinder of tetrafluoroethylene (TFE). The mixture was allowed to reach room temperature, the stirrer was turned on and TFE was pressured in at 35 psi.

The reaction was terminated after several days when the deep red color of the reaction mixture had turned to a light yellow color. Excess TFE and volatile products were vented, and the reaction mixture was poured into water. The iodine was destroyed with a solution of sodium bisulfite, and the product was separated as the heavy phase. The crude products of several runs were combined and distilled on an Oldershaw column. The average yield of the diiodide (b.p. 60°–61° C./13 mm) was 16 percent.

EXAMPLE III

Preparation of FCOCF$_2$OCF$_2$CF$_2$OCF$_2$COF

The diiodide CF$_2$ICF$_2$OCF$_2$CF$_2$OCF$_2$CF$_2$I (55 g, 0.99 mole), prepared as described in Example II, and ZnSO$_4$ (0.6 g) were added to a three-neck flask equipped with thermometer reflux condenser, magnetic stirrer, dropping funnel and gas inlet tube. The mixture was heated at 90° C. and fuming sulfuric acid (200 g, 65% SO$_3$) was added while a slow flow of chlorine was bubbled through the solution. The temperature of the reaction mixture dropped to 70° C. during addition of the sulfuric acid. After the addition was completed (30 minutes), the mixture was heated at 70° C., and the addition of chlorine was continued for an additional 45 minutes (total chlorine: 3 g, 0.04 mole).

After cooling to ambient temperature, the product separated as a clear colorless layer formed on top of the green-colored sulfuric acid layer. The crude product was recovered by decantation and then distilled to give 15 g of the product boiling at 72°–72° C. (66.6% yield). The structure of the product as shown above was confirmed by infrared and NMR analyses.

EXAMPLE IV

Preparation of FCOCF$_2$O(CF$_2$)$_5$OCF$_2$COF

A run was carried out in which the above product was prepared by following essentially the same procedure described in Example III. Thus, the diiodide CF$_2$ICF$_2$O(CF$_2$)$_5$OCF$_2$CF$_2$I (97 g, 0.13 mole), prepared as described in Example I, and ZnSO$_4$ (0.7 g) were heated at 90° C. and fuming sulfuric acid (300 g, 65% SO$_3$) was added while a slow flow of chlorine was passed through the solution. After the addition was completed (60 minutes), the mixture was heated at 70°–75° C. and the addition of chlorine was continued for an additional 90 minutes (total chlorine: 16 g, 0.23 mole). The crude product was recovered by decantation and then distilled to give the diacyl fluoride (b.p. 138°–139° C.) in 44.6% yield. The structure of the product as shown above was confirmed by infrared and NMR analyses.

As seen from the foregoing, the present invention provides a process for synthesizing symmetrical perfluoroalkylene oxide α,ω-diacyl fluorides, including products that could not be prepared by conventional prior art procedures. The diacyl fluorides are useful as intermediates in preparing perfluoroalkylene ether imidate and thioimidate esters which are monomers used in synthesizing bibenzoxazole polymers. Because they are thermally stable and have a low glass transition temperature, the polymers are eminently suitable for various aerospace applications, such as for seals and sealants.

As will be evident to those skilled in the art, various modifications of the present invention can be made in view of the foregoing disclosure without departing from the spirit and scope of the invention.

I claim:

1. A process for preparing symmetrical perfluoroalkylene oxide α,ω-diacyl fluorides which comprise the steps of heating a mixture of a diiodide and a catalytic amount of zinc sulfate at a temperature in the range of about 60° to 110° C., the diiodide having the following formula:

CF$_2$ICF$_2$O(CF$_2$)$_x$OCF$_2$CF$_2$I, where x is an integer greater than 2; adding fuming sulfuric acid to the mixture while bubbling chlorine therethrough; and recovering from the mixture a diacyl fluoride having the following formula:

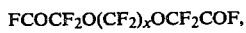

FCOCF$_2$O(CF$_2$)$_x$OCF$_2$COF, where x is an integer greater than 2.

2. The process according to claim 1 in which the mixture is maintained at a temperature in the range of about 60° to 110° C. for a period of about 2 to 8 hours.

3. The process according to claim 2 in which x is an integer in the range of 2 to 10, inclusive.

4. The process according to claim 3 in which the mole ratio of free sulfur trioxide contained in the fuming sulfuric acid to the diiodide ranges from about 8 to 20:1 and the amount of zinc sulfate ranges from about 0.5 to 5 weight percent, based upon the weight of the diiodide.

5. The process according to claim 4 in which the amount of chlorine added to the mixture ranges from about 5 to 20 weight percent, based upon the weight of the diiodide.